United States Patent [19]

Plint et al.

[11] Patent Number: 5,042,292

[45] Date of Patent: Aug. 27, 1991

[54] VISCOMETER

[75] Inventors: Michael A. Plint, Wargrave; Adrian G. Plint, Hamstead Marshall, both of United Kingdom

[73] Assignee: Plint and Partners Limited, Wokingham, United Kingdom

[21] Appl. No.: 479,391

[22] Filed: Feb. 13, 1990

[30] Foreign Application Priority Data

May 22, 1989 [GB] United Kingdom ............... 8911737
Sep. 29, 1989 [GB] United Kingdom ............... 8921994

[51] Int. Cl.$^5$ ............................................. G01N 11/14
[52] U.S. Cl. ......................................................... 73/60
[58] Field of Search ............................. 73/60, 59, 54

[56] References Cited

U.S. PATENT DOCUMENTS 2,568,793  9/1951  Beaumont ............................. 73/60
3,111,838 11/1963  Bucalo .................................. 73/54

FOREIGN PATENT DOCUMENTS 380995   6/1973  U.S.S.R. ................................ 73/59
648885  10/1977  U.S.S.R. .
823978   4/1981  U.S.S.R. ................................ 73/59
711899   7/1954  United Kingdom .................. 73/59

1589498  5/1981  United Kingdom .

OTHER PUBLICATIONS

"Some Suggestions for New Rheometer Designs: III. Anomalous Results for Highly Viscous Fluids", J. Phys. D: Appl. Phys, vol. 6, 1973, pp. 909–926.
"Kontinuierliche Viskositaetsmessung in der Betriebsmesstechik", Franz, E., Fette, Seifen, Anstrichmittel, Apr. 1971, p. 247.

Primary Examiner—Hezron E. Williams
Assistant Examiner—Joseph W. Roskos
Attorney, Agent, or Firm—St. Onge Steward Johnston & Reens

[57] ABSTRACT

A viscometer comprising a first member having an internal surface which is at least part-cylindrical, a second member which is cylindrical and is eccentrically mounted relative to the said internal surface, the first and second members defining therebetween a gap for receiving liquid to be tested, a drive means for causing relative rotation between the first and second members and pressure detecting means for detecting a pressure difference between liquid in a region of the said gap and liquid in a second region. The invention also provides a method of measuring viscosity.

5 Claims, 3 Drawing Sheets

VISCOMETER

BACKGROUND TO THE INVENTION

This invention relates to a viscometer which is a class of instrument commonly used for the measurement of the viscosity of liquids.

DESCRIPTION OF THE PRIOR ART

A known version of this instrument comprises a cylinder mounted concentrically in a cylindrical bore of larger size. The liquid of which it is desired to measure the viscosity fills the annular space between the cylinder and the bore. Arrangements are made to rotate the cylinder at a measured speed and to measure the torque required to effect this rotation. The viscosity of the liquid may be calculated directly from a knowledge of this torque, the rotational speed and the dimensions of the apparatus.

A disadvantage of instruments of this type is that the torque must be measured very precisely and the instrument is essentially only suitable for use in a clean laboratory environment.

British Patent Specification No. 1589498 discloses an apparatus for measuring viscosity of liquids incorporating an impelling element and a pressure transducer, the impelling element being operable to direct a periodically varying flow of liquid towards the transducer. The measured pressure variations can yield a value for the measured viscosity.

British Patent Specification No. 711899 discloses an apparatus for measuring viscosity of fluids comprising two relatively rotatable members which define therebetween a space for receiving fluid to be tested, a stationary obstruction member which is arranged in the space and means for measuring a pressure difference at two points of the space located on opposed sides of the obstruction member.

British Patent Specification No. 595023 discloses a viscosimeter comprising two relatively rotatable members defining an intervening space adapted to receive a viscous liquid, means for uniformly rotating one member relative to the other and means for measuring the pressure effect generated by the eddy movements of the viscous liquid.

SUMMARY OF THE INVENTION

The present invention provides a viscometer comprising a first member having an internal surface which is at least part-cylindrical, a second member which is cylindrical and is eccentrically mounted relative to the said internal surface, the first and second members defining therebetween a gap for receiving liquid to be tested, a drive means for causing relative rotation between the first and second members and pressure detecting means for detecting a pressure difference between liquid in a region of the said gap and liquid in a second region.

In one embodiment, the first member defines a chamber for receiving liquid to be tested, the chamber having an axis, the second member is disposed in the chamber and has an axis which is parallel to but offset from the axis of the chamber, and the pressure detecting means is adapted to detect a pressure difference between the first and second regions of liquid which are in the chamber.

Preferably, the pressure detecting means comprises two ports in the first member which are in communication with the chamber and a manometer which is connected to the two ports.

Preferably, the first member includes input and output ports for the chamber whereby the viscometer is arranged to measure viscosity of liquid flowing through the chamber.

In an alternative embodiment, the first member comprises an at least partial journal having an axis, the second member comprises a rotor which is disposed in the journal, the second member having an axis which is parallel to but offset from the axis of the journal, and the pressure detecting means is adapted to detect a pressure difference between liquid in the first-said region which is in the journal and liquid in the second region which is outside the journal.

Preferably, the viscometer further comprises means for mounting the first and second members immersed in liquid to be tested.

The viscometer may further comprise a temperature detecting means for detecting the temperature of the liquid under test.

The viscometer may still further comprise means for determining a viscosity value at a desired temperature, the means for determining being arranged to receive a signal from the pressure detecting means and a signal from the temperature detecting means.

The present invention further provides a method of measuring viscosity, the method comprising disposing liquid to be tested in the gap between the first and second members of a viscometer of the present invention, disposing liquid in a second region, relatively rotating the first and second members and detecting a liquid pressure difference between a region of the gap and the second region.

Preferably the liquid is arranged to flow through the gap.

BRIEF DESCRIPTION OF THE DRAWINGS

Embodiments of the present invention will now be described by way of example only with reference to the accompanying drawings, in which.

DETAILED DESCRIPTION OF THE PREFERRED EMBODIMENTS

Figure 2:
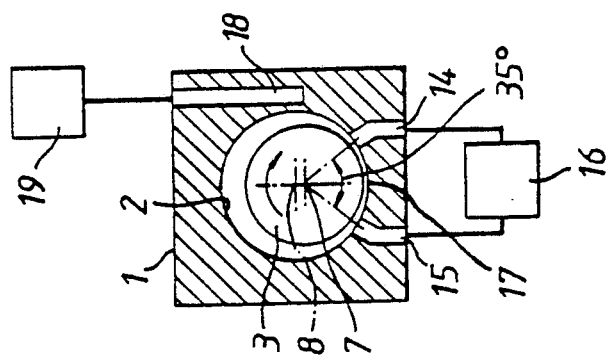
FIG. 2 shows a transverse section on plane A—A of FIG. 1.
Figure 1:
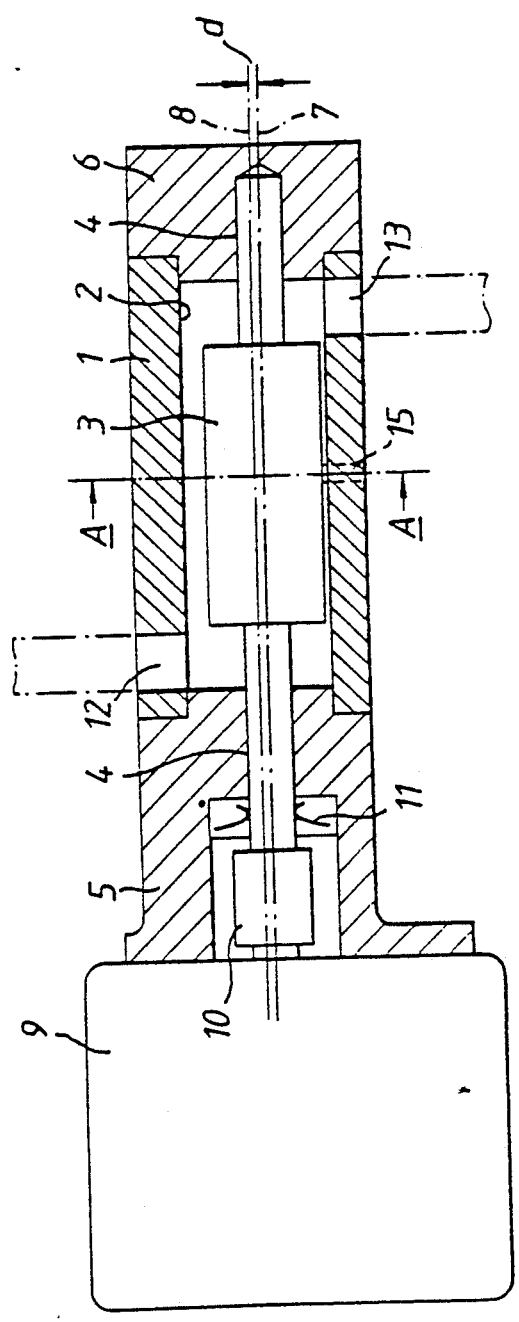
FIG. 1 shows a cross-section of a viscometer in accordance with a first embodiment of the present invention.

Referring to FIGS. 1 and 2, a viscometer in accordance with a first embodiment of the present invention comprises a casing 1 having an accurately finished cylindrical bore 2. A rotor 3 is carried in bearings 4 in end casings 5 and 6. The axis 7 of the rotor is displaced from the axis 8 of the bore 2 by a gap having a distance "d", shown exaggerated in the figures.

The rotor is driven at the desired speed by a motor 9 by way of a coupling 10. Leakage of the liquid is prevented by a seal 11.

The liquid, the viscosity of which is to be determined, is introduced through a port 12, fills the entire space within the viscometer and leaves by way of a port 13. This flow may if desired be in the reverse direction.

Figure 3:
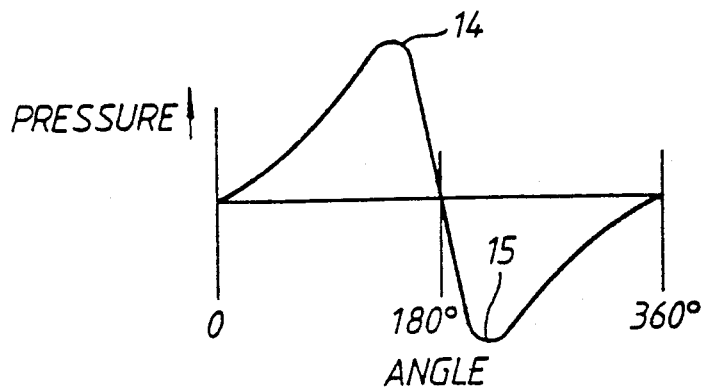
FIG. 3 is a graph showing the relationship between pressure and rotational angle in the viscometer of the first embodiment of the present invention.

FIG. 2 shows a transverse section through the instrument. When the rotor is in motion a pressure difference is generated around the circumference of the bore 2 of a form similar to that shown in FIG. 3. To detect the maximum value of these pressure differences, tappings 14 and 15 are made in the wall of the bore to sense the pressures developed at the corresponding points on the curve shown in FIG. 3. Typically these tapping points would be located at an angle of approximately 35 degrees on each side of the point of closest approach between the rotor and the cylinder bore.

The pressure difference is measured by a manometer 16 of any desired form which may comprise a pressure transducer with suitable electronic readout. In an alternative form of the device pressure, tapping 15 may be placed at location 17 in which case the pressure indicated is only the positive pressure difference generated on the converging side of the clearance. This arrangement can obviate possible problems with cavitation.

The temperature sensor 18 indicates the temperature of the casing 1 which for small rates of liquid flow is identical to that of the liquid. This temperature sensor may be connected to an indicator 19. Alternatively the temperature sensor may be immersed in the liquid.

The manometer 16 may be calibrated to give a direct indication of the dynamic viscosity of the liquid while with a suitable electronic circuit the signal from the temperature indicator 19 may be combined with that from the pressure indicator 16 to give a value of viscosity corrected to any desired temperature.

Figure 4:
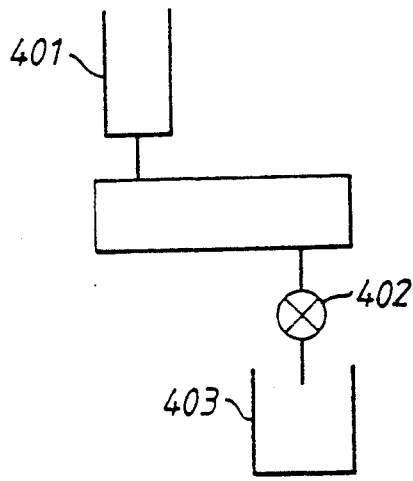
FIG. 4 shows schematically a first operational arrangement of the viscometer of the first embodiment of the present invention.

The instrument may be used in any of the following ways:

In FIG. 4 a vessel 401 is attached to the inlet port 12 and a needle valve 402 and collecting vessel 403 are attached to outlet port 13. With this embodiment the instrument may be used to measure the viscosity of a liquid sample.

Figure 5:
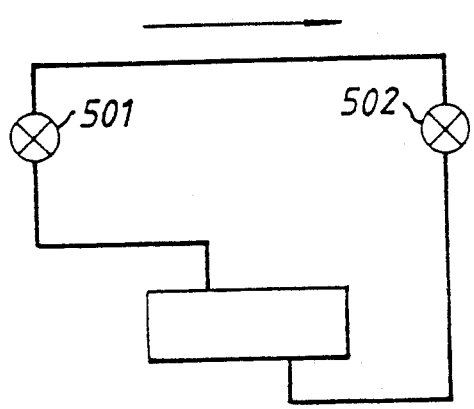
FIG. 5 shows schematically a second operational arrangement of the viscometer of the first embodiment of the present invention.

In FIG. 5 the instrument is installed in a bypass in a process line in which is flowing a fluid the viscosity of which is to be monitored. Valves 501 and 502 control the flow through the viscometer which may, if desired, be left permanently in circuit.

Figure 6:
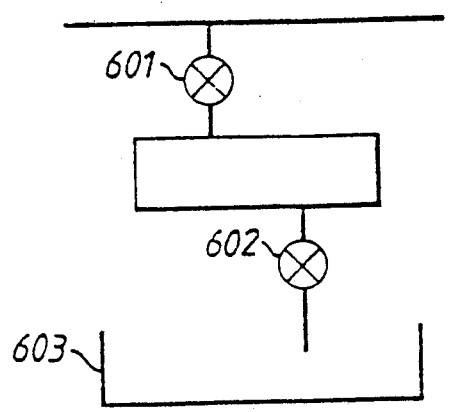
FIG. 6 shows schematically a third operational arrangement of the viscometer of the first embodiment of the present invention.

In FIG. 6 the viscometer is located in a branch in a process line, the flow being controlled by valves 601 and 602 and the discharge from the viscometer being returned to a sump 603. This arrangement is particularly suited to the monitoring of the viscosity of the lubricant in machines such as internal combustion engines.

Figure 7:
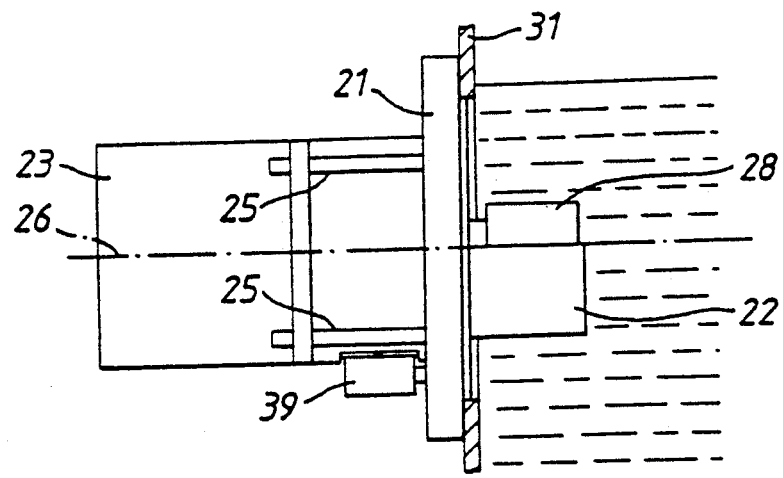
FIG. 7 show a perspective side view of a viscometer in accordance with a second embodiment of the present invention.
Figure 8:
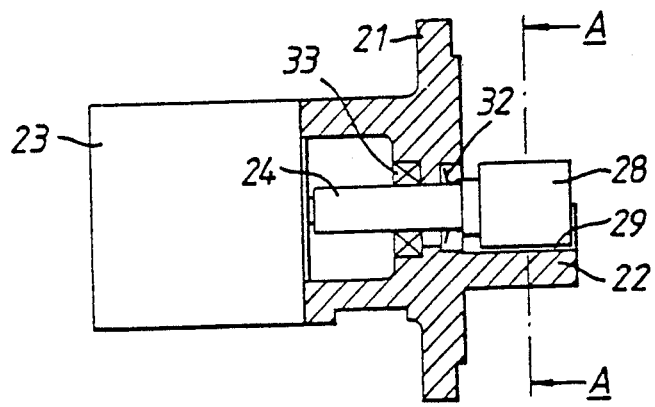
FIG. 8 shows a cross-sectional side view of the viscometer of FIG. 7.
Figure 9:
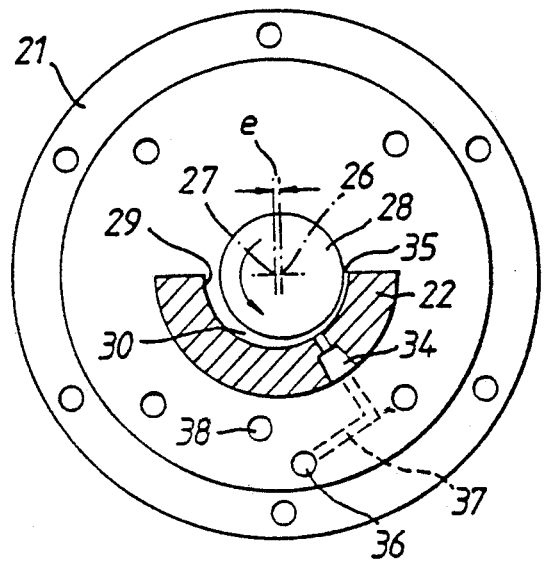
FIG. 9 is a cross-section on plane A—A of the viscometer of FIG. 8.

Referring to FIGS. 7 to 9, a viscometer in accordance with a second embodiment of the present invention comprises a flanged body 21 incorporating a half journal-bearing 22 and a motor 23 carrying a shaft 24, the motor 23 being attached to the flanged body 21 by mounting means 25, such as bolts. A bearing 33 supports the shaft 24 in the flanged body 21. The common axis 26 of the motor and shaft 23,24 is displaced from the axis 27 of the journal-bearing 22 by an eccentricity e, shown exaggerated in FIG. 9. The shaft carries a cylindrical rotor 28. A gap 30 is defined between the rotor 28 and the internal surface of the bore 29. The rotor is driven in the direction indicated by the arrow, thus ensuring that the gap 30 diminishes in the direction of motion.

The flange of the flanged body 21 is mounted on any suitable vessel, tank or pipe 31 in such a way that the rotor 28 and journal 22 are introduced into the liquid the viscosity of which is to be determined. The motor is disposed on the outside of the vessel 31 and a seal 32 is provided to prevent leakage of liquid from the vessel 31.

A pressure tapping 34 is provided in the journal 22 in advance of the position of closest proximity 35 between the rotor 28 and the journal 22. The pressure tapping 34 is taken to a suitable outlet 36 by means of a pipe 37. A second pressure tapping 38 into the body of the liquid in the vessel 31 is provided. A differential pressure transducer 39 is connected across the two pressure tappings 34,38 in order to indicate the difference in pressure between the free body of the liquid and the liquid within the journal-bearing 22.

In use, the rotor 28 and the journal 22 are immersed in liquid, and when the rotor 28 is set in motion by means of the motor 23 liquid will be entrained between the rotor 28 and the journal 22 and pressure will be generated in the gap 30 between the rotor 28 and the journal 22. At a given speed of rotation the difference in pressure between the liquid in the journal 22 and the liquid in the free-body of the liquid will be proportional to the viscosity of the liquid. The pressure difference is detected by the differential pressure transducer 39 thereby to output a reading which is directly related to the viscosity of the liquid.

The instrument may be used by being fitted directly into the sump or oil tank of any engine, gear-box or similar device in order to monitor continuously the viscosity of the fluid in the device.

Alternatively, the instrument may be fitted into a pipe-line in order to monitor the viscosity of the liquid flowing in the pipe-line.

The viscometer of the present invention differs from instruments of known type in that the inner cylinder or rotor is mounted eccentrically relative to the bore of the casing or of the journal, respectively. With this configuration when the inner cylinder or rotor is rotated substantial pressure differences may be developed between the inner cylinder, or rotor and the casing, or journal, respectively. It may be shown that the magnitude of the pressures so developed at a given speed of rotation bears a direct relationship to the viscosity of the liquid in the annular space between the bore and the inner cylinder or rotor; see for example "Fluid Mechanics", by M. A. Plint and L. Boswith, published by Griffin, page 126.

The pressure differences may thus be used as a direct means of measuring the viscosity of the liquid and since accurate measurement of pressure is a much simpler matter than accurate measurement of torque the instrument becomes more suitable for use in field conditions.

A further advantage of the invention is that the instrument may be used either to measure the viscosity of a small sample of liquid or to carry out continuous or intermittent measuring of the viscosity of a liquid flowing in a circuit.

What we claim is:

1. A viscometer comprising a first member comprising a half-bearing of semi-cylindrical form, a second member comprising a cylindrical rotor which is eccentrically mounted relative to the first member such that a space between the members forms a converging passage, a drive means for rotating the second member whereby, when liquid is present in the space, a pressure is generated between the two members and pressure detecting means which is adapted to detect a pressure difference between liquid at a point in the converging passage and liquid in a body of liquid lying outside the said passage.

2. A viscometer according to claim 1 further comprising a temperature detecting means for detecting the temperature of the liquid under test.

3. A viscometer according to claim 1 further comprising means for determining a viscosity value at a desired temperature, the means for determining being arranged to receive a signal from the pressure detecting means and a signal from the temperature detecting means.

4. A viscometer according to claim 1 wherein the said point in the converging passage is located at a position at which the pressure developed is a maximum.

5. A method of measuring viscosity, the method comprising disposing liquid to be tested in the converging passage between the first and second members of a viscometer according to claim 1, providing a body of liquid, rotating the second member and detecting a liquid pressure difference between liquid at the said point and the body of liquid.

* * * * *